United States Patent
Muz et al.

(10) Patent No.: US 6,991,607 B2
(45) Date of Patent: Jan. 31, 2006

(54) PROCESS AND DEVICE FOR MEASURING EXHALED AIR TO DETERMINE METABOLIC FUNCTION OF A LIVING BEING

(75) Inventors: Christof Muz, Reutlingen (DE); Edwin Muz, Reutlingen (DE)

(73) Assignee: Nicolay Verwaltungs-GmbH, Nagold (DE)

(*) Notice: Subject to any disclaimer, the term of this patent is extended or adjusted under 35 U.S.C. 154(b) by 208 days.

(21) Appl. No.: 10/464,858

(22) Filed: Jun. 19, 2003

(65) Prior Publication Data

US 2004/0097822 A1 May 20, 2004

(30) Foreign Application Priority Data

Jun. 21, 2002 (DE) .......................... 102 28 497

(51) Int. Cl.
*A61B 5/08* (2006.01)

(52) U.S. Cl. .................. 600/532; 600/531; 73/23.3
(58) Field of Classification Search ......... 600/529–538; 73/23.3
See application file for complete search history.

(56) References Cited

U.S. PATENT DOCUMENTS

| 3,981,176 | A |   | 9/1976  | Jacobs        |           |
|-----------|---|---|---------|---------------|-----------|
| 5,060,506 | A | * | 10/1991 | Douglas       | 73/24.01  |
| 5,214,966 | A | * | 6/1993  | Delsing       | 73/861.28 |
| 5,392,635 | A | * | 2/1995  | Cadet et al.  | 73/24.01  |
| 5,581,014 | A | * | 12/1996 | Douglas       | 73/24.01  |
| 6,076,392 | A | * | 6/2000  | Drzewiecki    | 73/23.2   |

FOREIGN PATENT DOCUMENTS

| EP |        44596 A1 | * | 1/1982 |
| WO | WO 9313414 A1 | * | 7/1993 |

\* cited by examiner

*Primary Examiner*—Robert L. Nasser
*Assistant Examiner*—Navin Natnithithadha

(57) ABSTRACT

A process and a device are provided for determining the proportion of a component of the air exhaled by a breathing living being that is characteristic of the metabolic function of such living being. The invention relates to a process for determination of a first component $A_{a,1}$ in the air exhaled by a patient that is characteristic of the metabolic function of the patient such as carbon dioxide ($CO_2$) or oxygen ($O_2$), where the exhaled air having at least two components (i=1, 2, ...) each having a proportion $A_{a,i}$. The molecular weights $M_i$ and the adiabatic coefficients $k_i$ of the components are known. The process measures the velocity of sound $v_S$ in the exhaled air, and the portion $A_{i,1}$ of the first component in the exhaled air is calculated by use of the measured velocity, at a temperature T of the exhaled air. The proportion of the component is determined by the equation $M_G/k_G = R \times T/(v_s^2)$, where $M_G = \text{sum}(A_{a,i} \times M_i)$, i=1, 2, ..., and where $M_G$ is the molecular weight of the exhaled air, and $1/(1-k_G) = \text{sum}(A_{a,i}/(1-k_i))$, i=1, 2, ..., where $k_G$ is the adiabatic coefficient, and R is the universal gas constant.

14 Claims, 2 Drawing Sheets

PROCESS AND DEVICE FOR MEASURING EXHALED AIR TO DETERMINE METABOLIC FUNCTION OF A LIVING BEING

FIELD OF THE INVENTION

The present invention relates to a process for determining a portion of a component of the air exhaled by a breathing living being characteristic of the metabolic function of the living being. The invention is also directed to a device for determining the metabolic function of an animal by determining the composition of the air exhaled by the animal.

BACKGROUND OF THE INVENTION

The portion of carbon dioxide ($CO_2$) in exhaled air is an important variable that can be measured as an alternative or in addition to electrocardiography or measurement of the oxygen saturation of the blood, both for diagnostic purposes and for continuous monitoring over a protracted period in the intensive care unit of a hospital or in the sleep laboratory. The processes disclosed in EP 0 309 666 A1, DE 39 36 825 C2, or U.S. Pat. No. 5,159,934 disclose processes for determining of the $CO_2$ content of respiratory air by measuring the absorption of infrared radiation.

In the so-called "mainstream process", the detector that measures the absorption of the infrared radiation is mounted directly in the airway of the patient. This presents the disadvantage that the result of measurement may give false readings by precipitation of moisture onto the optical elements. In the so-called "sidestream process", a small part of the exhaled air is withdrawn and subjected to spectroscopic measurement by a device that is remote from the patient. Aside from the danger of possible obstruction of the suction hose, this process presents the disadvantage that slight variations in the $CO_2$ concentration, which may contain information of importance for diagnosis, generally cannot be detected in practice by metrological means.

EP 0 653 919 B1 and CH 669 463 A5 disclose a process and/or a device for measurement of flow rate, volume of flow, temperature, and mean molecular weights of gases and mixtures of gases. To the extent that measurement of molecular weights is used for the determination of various exhalation parameters in pulmonary function diagnosis, these documents teach the use a separate sensor for determination of the carbon dioxide or oxygen concentration.

SUMMARY OF THE INVENTION

Hence, the invention is directed to providing a process cad an associated device which overcome(s) the disadvantages of the state of the art. In particular, the determination of a component that is characteristic of the metabolic function is permanently reliable and is possible at high measurement rates. The associated device of the invention can be produced and operated coat effectively and is rugged and easy to clean.

In addition, this device is of low weight and sterilizable with superheated steam.

The disadvantages of the prior processes at overcome by a process for the determination of the portion $A_2$ of a first component that is characteristic of the metabolic function of a breathing living being in their exhaled by the living being. In particular, the portion of carbon dioxide ($CO_2$) and/or oxygen ($O_2$) is determined in the exhaled air. The exhaled air has a minimum of two, but generally four, components (i =1, 2, ... ), each having a portion $A_{a,1}$. The molecular weights $M_i$ and the adiabatic coefficients $k_i$ of the components are known constants. The velocity of sound $v_S$ is measured in the exhaled air. The portion $A_{a,1}$ of the fast component in the exhaled air is measured by use of the velocity of sound $v_S$, the temperature T of the exhaled air, and the relation $M_G/k_G = R \times (T/v_S)$, $M_G$=sum of $(A_{a,i} \times M_i)$, i=1, 2 ... where $M_G$ is the molecular weight of the exhaled air, $1/(1-k_G)$= sum of $A_{a,1}/(1-k_i)$, i=1, 2, ... to the adiabatic coefficient $M_G$ of the exhaled air, and R is the universal gas constant.

The various aspects of the invention will become apparent from the annexed drawings and the following detailed description of the invention.

BRIEF DESCRIPTION OF THE DRAWINGS

The following is a brief description of the drawings, in which.

DETAILED DESCRIPTION OF THE INVENTION

Figure 1:
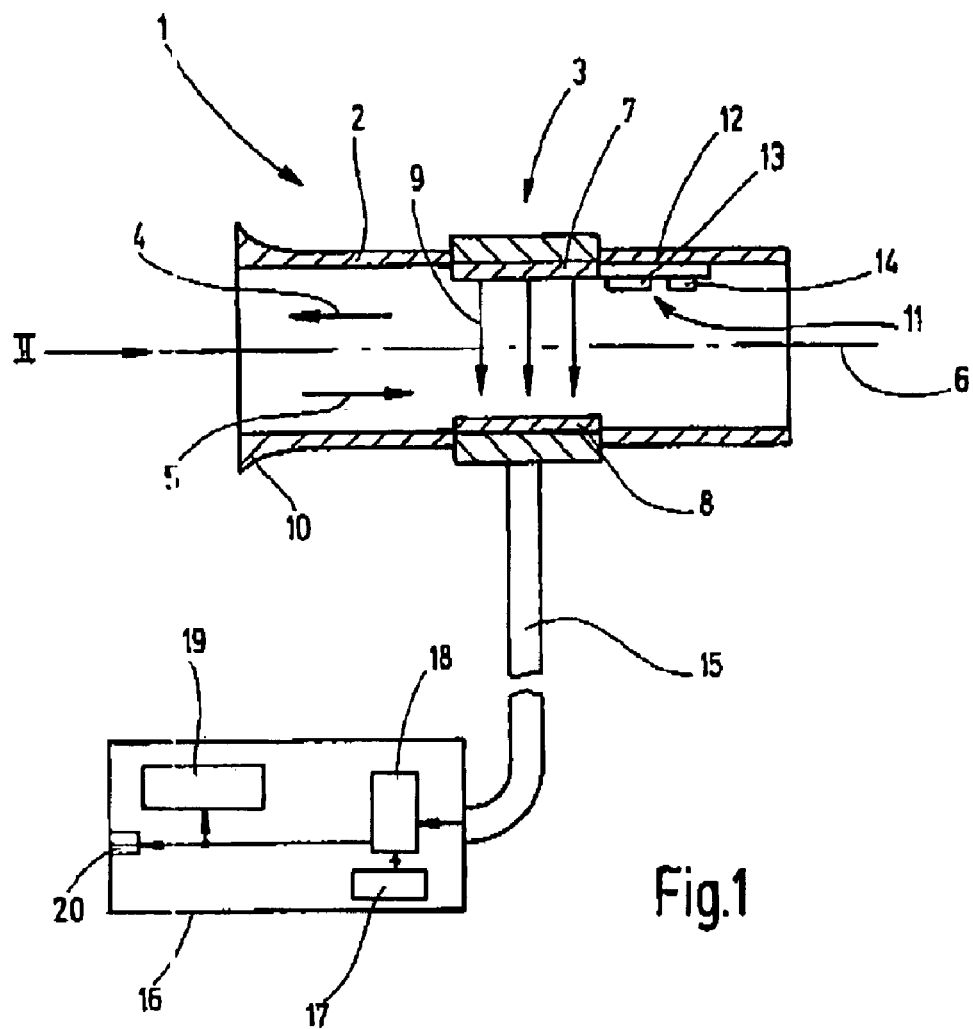
FIG. 1 is a side view in cross-section of a first exemplary embodiment of the invention.

The process and device of the invention afford, among others, the advantage that the adiabatic coefficient $k_G$ for the gas mixture of the exhaled air do not need to be precisely calculated or determined with precision empirically. Rather, it suffices for the quotient of molecular weight $M_G$ and adiabatic coefficient $k_G$ to be determined at known temperature 7 in accordance with the relation indicated after metrological determination of the velocity of sound.

Except as otherwise indicated herein, the portions of the components always represent portions of volume by percent in relation to the total volume of air inhaled or exhaled. In principle, both inhaled and exhaled air contain moisture. The moisture content is generally higher in the case of exhaled air than in that of inhaled air.

In principle, the determination of both the proportion of carbon dioxide and the proportion of oxygen as a characteristic component is considered. Since, however, the relative changes in the portions between inhaled and exhaled air are generally greater in the case of carbon dioxide than in that of oxygen, preference is given to this consideration without restricting the generality of the invention.

Under normal environmental conditions, the portion $A_{ct,1}$ of the first component carbon dioxide ($CO_2$) amounts to 0.034%, for dry air (moisture content=0). The portion $A_{ct,2}$ of the second component oxygen ($O_2$) typically amounts to 20.95%. The portion $A_{ct,3}$ of the third component, inert gases, and nitrogen ($N_2$) in particular, typically amounts to 79.015%. These portions occur naturally and are known. The fourth component is water vapor or moisture. The moisture content of inhaled air is calculated from the ambient temperature. The relative humidity and the air pressure are determined by the device of the invention, by measurement of the velocity of sound, to determine whether variations from this composition are present. The universal gas constant R amounts 8.314 Ws/(K×mol).

The molecular weight $M_G$ of the gas mixture of exhaled air is determined from the sum of the products of portions $A_{a,i}$ of the individual gas components of the exhaled air and the molecular weight. $M_i$ of the individual gas components.

The molecular weights are known and maybe taken for the appropriate technical literature. The adiabatic coefficient $k_G$ of the gas mixture of exhaled air is to be determined by the portions $A_{a,i}$ of each of the components of the exhaled air by means of the known adiabatic coefficients $k_i$ of the respective components of the exhaled air. The adiabatic coefficients $k_i$ are known and may be taken, for example, from the technical literature. Consequently, the equations indicated may be linked to each other in such a way that a specific solution for the portion $A_{a,1}$ of the first component may be determined if it is assumed that the volume of the inert gas is equal in the inhaled and the exhaled air and an estimate is adopted for the respiration quotient RQ.

In one particular embodiment of the invention the sum of the portion $A_{a,1}$ of the first component and a portion $A_{a,2}$ of a second component of the exhaled air more or less equals the sum of the portions $A_{ct,1}$ and $A_{ct,2}$ of the inhaled air, which are known or may be measured separately. In particular, the sums of the carbon dioxide and oxygen portions of the dry air portion of inhaled and exhaled air are more or less of equal value.

The respiration quotient RQ is defined as the volume of carbon dioxide given off relative to the volume of oxygen absorbed and according to data in the literature ranges from 0.7 or 0.8 to 1, depending for example, on the state of the health of the patient. Consequently, the volume exhaled is smaller than the volume inhaled for a respiration quotient RQ smaller than 1.

Allowance for this circumstance is made as follows in the calculation algorithm. $V_n + V_c$ is the average respiration volume standardized with respect to temperature and humidity, with $V_c$ for the inhaled and $V_a$ for the exhaled air volume. For example, the respiration volume is standardized to a humidity of 0%, that is, dry air, and a predetermined temperature such as body temperature. The same applies correspondingly to the inert gas.

$$V_c \times A_{ct,3} = V_{ct,3}$$

or, with a factor f introduced, $$A_{ct,3} = f \times A_{ct,3} \text{ or}$$

$$f^{a+1} A_{ct,3} / A_{ct,3} = V_e / V_3$$

Hence, it is advantageous if, in an embodiment of the process of the invention, the inert gas portion of the exhaled air is set to equal the inert gas portion of the inhaled air multiplied by the factor f.

The difference between inhaled and exhaled volume is described by the formula $$V_c - V_8 = (A_{ct} + A_{ct,2} + A_{ct,3}) \times V_c - (A_{ct,1} + A_{ct,2} + A_{ct,3}) \times V_3$$

and if the portion $A_{ct,1}$ of the inhaled carbon dioxide in dry air is disregarded ($A_{et,1} = 0$) and if allowance is made for the volume of the inert gas component not varying during respiration ($A_{ct,3} \times V_c = A_{ct,3} 2$), then $$V_c - V_a = A_{ct,2} \times V_c - (A_{ct,1} - A_{ct,2}) \times V_a.$$

Together with the equation for the respiration quotient RQ, to which applies the formula $$RQ = A_{ct,1} \times V_a (A_{ct,2} \times V_a),$$

with the portion $A_{ct,1}$ disregarded, there is obtained the relation $$f = 1 - A_{ct,1} \times (1/RQ - 1),$$

by means of which the ratio $V_c / V_a$ may be estimated. When RQ = 1, f = 1, and when RQ = 0.8, with $A_{ct,1}$. 0.06, l' = 1.02.

Adequate accuracy is attained for many applications if the calculation is performed for factor f with a value corresponding to a respiration quotient RQ of 0.85. Should more precise measured values of the carbon dioxide concentration be required, inhaled and exhaled volume may be determined metrologically and factor f calculated precisely.

The portion of a fourth component, moisture, generally present in exhaled air, may be assumed for many applications to be saturated water vapor. The portion of moisture is accordingly determines by the temperature T of the exhaled air and the barometric air pressure $P_{bar}$.

It may be sufficient for many applications to adopt the body temperature of the living being that is being examined as the temperature T of the exhaled air. This body temperature may either be determined separately by metrological means, an empirically ascertained value maybe used for which the specific measuring instrument setup is taken into account, or a conventional value may be adopted, such as the average body temperature of 37° C.

If greater measurement accuracy is required, the temperature T of exhaled air may also be determined directly by metrological means. Numerous measurement processes, such as ones involving use of thermocouples or temperature dependent resistors, are commercially available for this purpose.

It may be advantageous for many applications, however, to determine the temperature T of the exhaled air metrologically with a dewpoint sensor. In this process, the temperature of a bedewed surface a adjusted so that moisture precipitate is formed and is still perceptible. The moisture may be determined in various ways, such as optically from a modified reflection or transmission pattern, or on the basis of change in an electric resistance, in electric capacitance, or in mechanical oscillation properties.

Preferably, an ultrasound signal, such as one having a frequency ranging from 50 to 200 kHz, especially around 120 kHz, is used for measurement of the velocity of sound $v_3$. The velocity of sound is measured more or less at a right angle to the main direction of flow of the exhaled air. As a result, incidental effects are eliminated, for example, effects such as air turbulence which may occur during inhalation and exhalation. The measured value of the velocity of sound $v_S$ may be verified by also measure the velocity of sound of the inhaled air, the composition and calculating the expected, velocity of sound. The measured value of the velocity of sound $v_S$ of the exhaled air is considered to be valid only if the value measured for the inhaled air is in sufficiently close agreement with the expected value.

The disadvantages of the prior devices are overcome by the device of the present invention. The device of the invention has a first measuring system for measurement of the velocity of sound $v_S$ of the exhaled air, electronic storage means for storage of the molecular weights $M_1$ and adiabatic coefficients $k_i$ of the components of the respiratory air, and electronic computing means for calculation of the portion $A_{g,1}$ of the first components. The electronic computing means and electronic storage means may preferably be configured in one module and, for example, as a plug-in card for a commercially available personal computer or for basic medical equipment as known in the art. The values forte molecular weights $M_i$ and/or the adiabatic coefficients $k_i$ may the permanently set or programmable or predetermined.

In one particular embodiment of the invention the first measuring system with a first measurement axis is mounted in a respiration tube between a mouthpiece and an opening through which the exhaled air may be expelled. The measuring means of the first measuring system are preferably mounted on opposite sides of the respiration tube. The first measurement axis for measurement of the velocity of sound $v_S$ preferably is oriented so that it forms a more or less right angle with the longitudinal axis of the respiration tube in the area of the first measuring system.

In one particular embodiment of the invention, the device has a second measuring system with a second measurement axis in the respiration tube, which is mounted so that the second measurement axis forms as acute angle with the longitudinal axis of the respiration tube in the area of the second measuring system. The first and second measurement axes preferably form a more or less right angle. The second measuring system may be used in particular for metrological determination of the volume of the inhaled air and/or the exhaled air and accordingly of the ratio $f=V_c/V_a$. In addition, the second measuring system may be used to determine other parameters of the respiratory air, such as the volume flow or the rate of flow.

In one particular embodiment, the temperature of the exhaled and/or inhaled air is measured by means or a sensor. Use is preferably made for this purpose of a dewpoint sensor the temperature of which is set so that the moisture in the gas surrounding the sensor begins to condense. If desired, both a dewpoint sensor and a temperature sensor maybe used.

An exemplary embodiment of the process of the invention is described with reference to an independently breathing patient. In this case it is to be stipulated that the composition of the inhaled air is known. If the portions of the inert components of the air, those of nitrogen and other inert gases in particular, are combined in one inert gas mixture which does not undergo chemical change during the process of respiration, the portions of the inhaled, dry air in terms of volume in relation to the total volume of the inhaled air may be stated as follows:

| | |
|---|---|
| carbon dioxide: | $A_{ct,1}$ = 0.034% |
| oxygen: | $A_{ct,2}$ = 20.950% |
| inert gases: | $A_{ct,3}$ = 79.015% |
| moisture: | $A_{ct,4}$ = 0% |

The following are obtained for the portions of exhaled air by volume for the present exemplary embodiment:

The body temperature of the patient is adopted for the temperature T of the exhaled air. Saturation is assumed for the moisture content of the exhaled air. Consequently, the saturation pressure $P_S$ of the moisture or of the water vapor contained in the exhaled air depends exclusively on the temperature T and may be calculated by means of the so-called Magnus formula. For example:

$$P_S \text{ in millibars} = 6.112 \times \exp(17.62 \times T/(243.12 + T)) \qquad (1)$$

The known or measured barometric air pressure $P_{bar}$ is used to calculate the partial pressure and accordingly the portion by volume $$A_{a,4} = P_x/P_{bar} \qquad (2)$$

of the water vapor or the moisture as a function of the temperature T. The portion by volume of the inert gas is $$A_{a,3} = f \times A_{et,3} \times (1 - A_{a,4}) \qquad (3)$$

The portion $A_{a,1}$ of the carbon dioxide by volume is the quantity sought. The portion $A_{1,2}$ of the oxygen may be stated as $$A_{2,2} = 1 - A_{0,1} - A_{0,3} - A_{0,4} \qquad (4)$$

The following equation $$v_S = \sqrt{(k_G \times R \times T / M_G)} \qquad (6)$$

in which $k_G$ is the adiabatic coefficient of the gas mixture, R is the universal gas constant, and $M_G$ the molecular weight of the gas mixture, is valid for the measured velocity of sound $v_S$. The quotient of molecular weight $M_G$ and adiabatic coefficient $k_G$ as a function of temperature T and the measured velocity of sound $v_S$ maybe expressed by transposition of this equation:

$$M_G/k_G = R \times T/(v_S^2) \qquad (6)$$

The portion $A_{a,1}$ of the carbon dioxide to be determined may then be determined for each individual measured value of the velocity of sound $v_S$, the following statement applying to the molecular weight $M_G$:

$$M_G = \text{sum of all values } i\ (A_{a,i} \times M_i), \text{ with } i=1, 2, 3, 4 \qquad (7)$$

while the following applies to the adiabatic coefficient $k_G$;

$$1/(1-k_G) = \text{sum of all values } i(A_{a,i}/(1-k_i)) \text{ with } i=1,2,3,4 \qquad (8)$$

Equations (1) to (8) make up a system of equations with an unequivocal solution for the portion $A_{a,1}$ of the carbon dioxide as a function of the velocity of sound $v_S$, and temperature T. Consequently, it is necessary to know only the velocity of sound $v_S$, the barometric air pressure $P_{bar}$, and the temperature T of the air in the respiratory passage with the highest possible accuracy. The calculation may be performed with commercially available computing means, for example, also with a personal computer which executes an appropriate measuring and/or computing program.

FIG. 1 presents a side view in cross-section of a first exemplary embodiment of the device 1 of the invention for the determination of a portion of a component of the air exhaled by a living being that is characteristic of the metabolic function of the patient, in one embodiment, the device determines the portion of carbon dioxide in the air exhaled by a human patient.

In the first exemplary embodiment, a first measuring system 3 is mounted in a more or less cylindrical respiration tube 2 for determination of the velocity of sound $v_S$ of the respiratory air flowing through the respiration tube 2. The principal direction of flow of inhaled air is indicated by the arrow 4 and that of exhaled air by the arrow 5. The directions of flow extend more or less parallel to the longitudinal axis of the respiration tube 2. On opposite sides of the tube 2 relative to the longitudinal axis 6, the fast measuring system 3 has an ultrasonic sensor having a transmitter 7 and an associated receiver 8. The transmitter 7 transmits a signal having a predetermined signal shape, which is received and registered at the receiver 8. The velocity of sound $v_S$ of the respiratory air is determined from the transit time and the known distance between transmitter 7 and receiver 8. The first measurement axis 9 forms a right angle with the longitudinal axis 5 of the respiration tube 2.

One end of the respiration tube 2 has a mouthpiece 10 which is integrated with the tube as shown or can be removable, especially for cleaning purposes. The opposite end of the respiration tube 2 is open and respiratory air may flow in or out freely through the associated opening.

A sensor element 11 is mounted in the respiration tube 2, in the immediate vicinity of the first measuring system 3. In one embodiment, the sensor element can be connected to the first measuring means 3 by an electric connection. The sensor element 11 has a dewpoint sensor 13 with a temperature sensor 14 on an electrically heatable substrate 12. The substrate 12 is heated to a temperature each that a moisture precipitate (water droplets) is formed on the dewpoint sensor 13 that can be detected by the sensor 13. The temperature sensor 14 measures the pertinent temperature from which the portion of moisture in the respiratory air is in turn derived in accordance with the Magnus formula referred to above.

The electric signals are delivered over a connecting line 15 to an evaluation unit 16, which can be remote from the patient examined. This evaluation unit 16 has electronic storage means 17 to store the coefficients and constants required for calculation. The electronic storage 17 is programmable and thus may be updated. In addition, the evaluation unit 16 also has electronic computing means 18 connected to display unit 19 for displaying the calculated results and/or to a connecting element 20 for forwarding data to a downstream unit.

Figure 2:
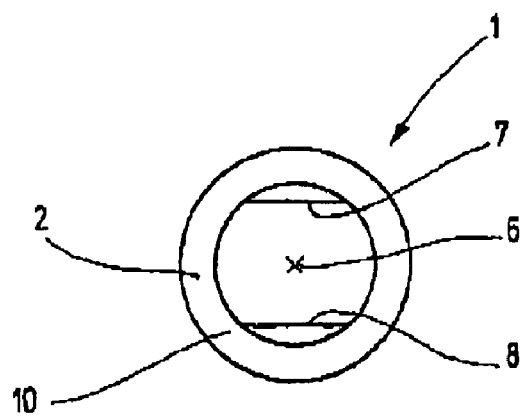
FIG. 2 is a front view along line II toward the device shown in FIG. 1.

FIG. 2 presents a front view along line II to the device shown in FIG. 1 in the direction of the longitudinal axis 6. The substantially cylindrical cavity is the respiration tube 2 is interrupted only in the area approximately central in the axial direction by the transmitter 7 and receiver 9, which preferably are mounted in parallel planes relative to each other.

Figure 3:
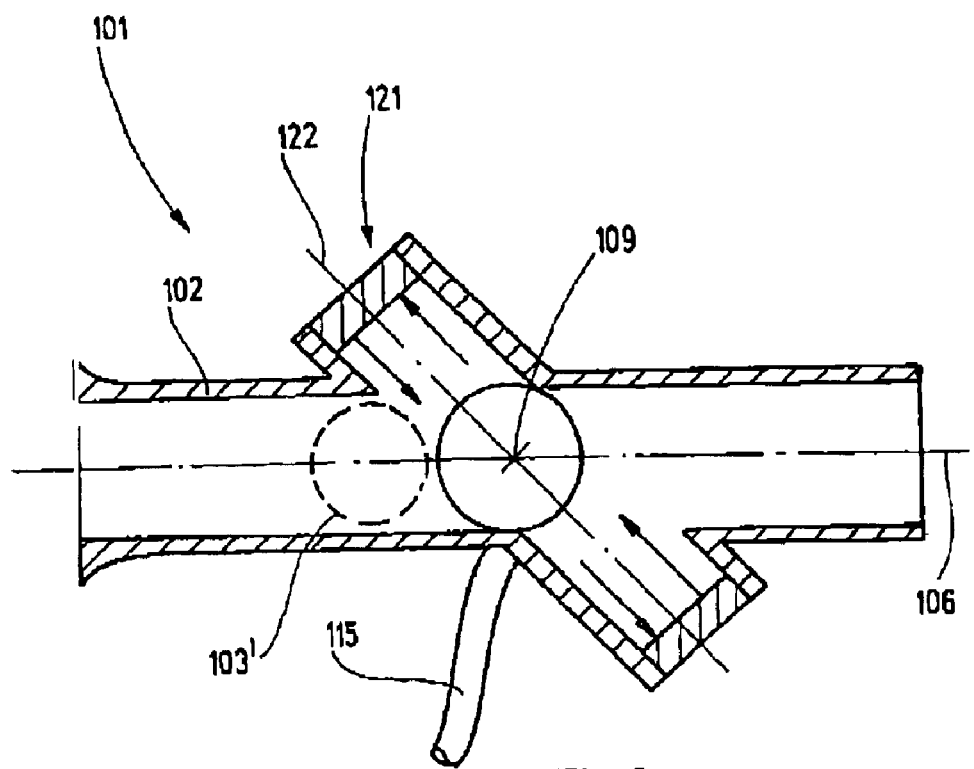
FIG. 3 is a top view in cross-section of a second exemplary embodiment of the invention.

FIG. 3 is a top view of a cross-section of a second embodiment 101 of a device of the invention. The first measuring system (not shown in detail in FIG. 3) has the first measurement axis 109 extending; perpendicular to the plane of the drawing. As has been specified in the foregoing, the portion $A_{a,1}$ of the first component in question of the gas mixture of the respiratory air is thereby determined.

The volume of inhaled and exhaled air is determined by a conventional method by a second measuring system 121 whose measurement axis 122 forms with the longitudinal axis 106 of the respiration tube 102 an acute angle 45°, for example. On the basis of the numerical values involved obtained for the respiration quotient RQ, which also depends among other things on the nutritional habits of the patient examined and may range from 0.7 to 1, the ratio f of inhaled to exhaled volume of the air standardized with respect to temperature and humidity is between 1 and 1.025. A fixed value of 1.01, for example, which yields adequate measurement accuracy for many applications, may be adopted for factor f in place of the ratio which may be determined with precision by the second measuring system 121. The signals of the first and second measuring systems 3,1 21, as well as those of any sensor elements present 7, may be transmitted over a common connecting line 115.

In the second exemplary embodiment shown, the first and second measurement axes 109, 122 intersect. It may be preferable for many applications to mount the fast measurement axis 109 offset a certain distance, especially in the direction of the longitudinal axis 206, from the second measurement axis 122. By preference the offset of the first measurement axis 109 toward the mouthpiece of he respiration tube 102 is, for example, 1 to 5 cm, in particular 2 to 3 cm, as is indicated by a broken line in FIG. 3 for the first measuring system 103'. As a result, interference of the measuring process of the first and second measuring systems 103',121, for example, may be prevented.

Figure 4:
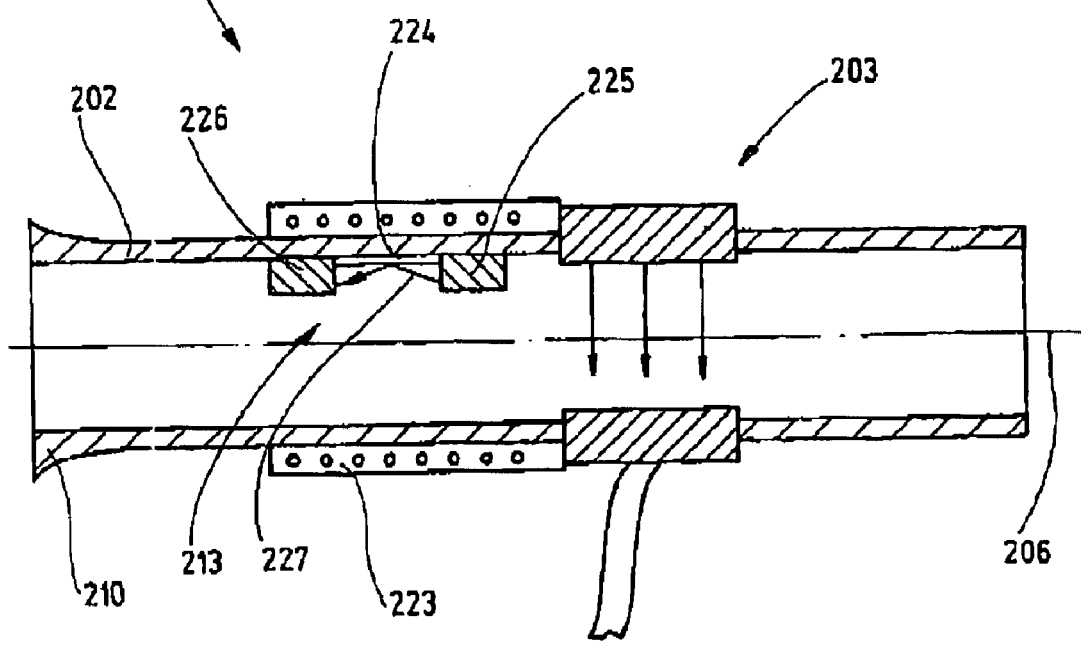
FIG. 4 is a side view in cross-section of a third exemplary embodiment of the invention.

FIG. 4 presents a side view of a cross-section of a third exemplary embodiment 201 of a device claimed for the invention. The device 201 differs from the first embodiment shown in FIG. 1 among other things in that the dewpoint sensor 213 is mounted between the first measuring system 203 and the mouthpiece 210 of the respiration tube 202. The dewpoint sensor 213 is heated by an annular beating sleeve 223. The moisture precipitate on a reflecting precipitate surface 224 is detected by evaluation of the optical reflection pattern. For this purpose an optotransmitter 225, such as a light emitting diode, directs a light beam 227 at an acute angle to the precipitate surface 224. Optimal reflection by the optoreceiver 226, such as a photodiode, is obtained if no moisture precipitate is present on the precipitate surface 224.

The temperature of the precipitate surface 224 is adjusted so that the smallest amount of sufficient precipitate is formed which can still be detected with certainty by the optoreceiver 226. The reflecting effect of the precipitate surface 224 may be obtained, for example, by appropriate metal coating of the surface. The configuration of the precipitate surface 224 may be oblong or substantially puncrate. In any event it is preferably positioned between the optotransmission element 225 and the optoreceiver 226. In order for the precipitate surface 224 to be positioned to the greatest extent possible in the direct airstream of the respiratory air in the respiration tube 202, the optotransmitter 225 and the optoreceiver 226 may be mounted so as to be offset from each other relative to the longitudinal axis 206, so that, they are not aligned with each other as the device 201 is viewed from the top, in the direction of the longitudinal axis 206 but rather are offset a certain distance in the circumferential direction.

As an alternative to the optically operating dewpoint sensor shown, a moisture precipitate may also be detected by evaluating the change in an electric resistor, an electric capacitance, or the mechanical oscillatory pattern. The temperature at which a still measurable moisture precipitate occurs is employed as the temperature T of the respiratory air. If necessary, allowance may be made for n correction factor or correction value, one obtained by empirical means, for example.

While various embodiments have been chosen to illustrate the invention, it will be understood by those skilled in the art that various changes and modifications can be made without departing from the scope of the invention as defined in the appended claims.

What is claimed is:

1. A device for measuring a metabolic function of a patient, said device comprising:

a first measuring system for measuring velocity of sound $v_S$ in exhaled air from a patient;

an electronic storage device for storing a molecular weight $M_i$ and an adiabatic coefficient $k_G$ of at least two gas components of the exhaled air; and an electronic computer connected to said first measuring system for receiving a signal corresponding to a measured velocity $v_S$ and for calculating a proportion $A_{a,1}$ of a first gas component of the exhaled air based on a measured velocity $v_S$, said first gas component being selected from the group consisting of oxygen and carbon dioxide, said computer being adapted to calculate the proportion of said first gas component in exhaled air by the formula $$M_G/k_G = R \times T/(v_S^2)$$

where $M_G$ is a molecular weight of the exhaled air, $k_G$ is an adiabatic coefficient of the exhaled air, R is a universal gas constant, and T is a temperature of the exhaled air, and by the formula $$M_G = \mathrm{sum}(A_{a,i} \times M_i)$$

where i is an integer corresponding to a number of gas components of the exhaled air, and $$1/(1-k_G) = \mathrm{sum}(A_{a,i}/(1-k_G))$$

where $k_i$ is the adiabatic coefficient of the gas components of the exhaled air.

2. The device of claim 1, further comprising a respiration tube having a passageway, a month piece at a first end and an opening at a second end for discharging the exhaled air;
said first measuring means is mounted on opposite sides of said respiration tube for measuring the velocity of sound along an axis substantially perpendicular to a longitudinal axis of said respiration tube.

3. The device of claim 2, further comprising a second measuring system mounted in said respiration tube to measure a volume of the exhaled air, said second measuring system being positioned to measure the volume along an axis at an acute angle with the longitudinal side of said respiration tube and at substantially a right angle with respect to said axis of said first measuring system.

4. The device of claim 1, further comprising a temperature sensor to measure the temperature of inhaled or exhaled air through said respiration tube.

5. The device of claim 4, wherein said temperature sensor is a dew point sensor.

6. A method for determining a portion $A_{a,1}$ of a first gas component in air exhaled by a breathing patient as an indication of metabolic function of the patient, the process comprising the steps of:
measuring a velocity of sound $v_S$ in the air exhaled from the patient, and
calculating the proportion $A_{a,1}$ of the first gas component in the air exhaled from the measuring of velocity $v_S$ by calculating using the formula:

$$M_G/k_G = R \times T/(v_S^2)$$

where the first gas component is carbon dioxide or oxygen in the air exhaled, $M_G$ is a molecular weight of the air exhaled, $k_G$ is an adiabatic coefficient of the air exhaled, R is an universal gas constant, and T is a temperature of the air exhaled, and where $$M_G = \mathrm{sum}(A_{a,i} \times M_i)$$

where
i is an integer corresponding to a number of gas components in the air exhaled, $M_i$ is a molecular weight of the i-th gas component in the air exhaled, $A_{a,i}$, is the proportion of the i-th gas component in the air exhaled, and $$1/(1-k_G) = \mathrm{sum}(A_{A,i}/(1-k_i))$$

where $k_i$ is the adiabatic coefficient of the i-th component in the air exhaled.

7. The method of claim 6, wherein the proportion $A_{A,1}$ of the first gas component of the air exhaled air is calculated by considering that the sum of the proportion $A_{a,1}$ of the first gas component and a proportion $A_{A,2}$ of a second gas component of the exhaled air substantially equals the sum of the proportions $A_{c,1}$, $A_{a,2}$, where $A_{a,1}$ and $A_{c,2}$ are proportions of first and second components of inhaled air.

8. The method of claim 6, wherein said proportion $A_{a,1}$ of the first gas component of the air exhaled is calculated based on a third gas component of air inhaled and exhaled air being inert.

9. The method of claim 6, wherein said calculation of the proportion $A_{a,1}$ of the first component of the air exhaled, includes a proportion $A_{a,4}$ of moisture contained in the air exhaled based on saturated water vapor, and wherein the proportion $A_{a,4}$ of the moisture is derived from the temperature T of the air exhaled.

10. The method of claim 6, further comprising measuring a temperature T of the air exhaled.

11. The method of claim 10, wherein the temperature T of the air exhaled is measured with a dewpoint sensor.

12. The method of claim 6, wherein the velocity of sound $v_S$ is measured with an ultrasonic signal.

13. The method of claim 6, comprising measuring the velocity of sound $v_S$ substantially at a right angle to the direction of principal flow of the air exhaled.

14. The method of claim 6, comprising measuring the velocity of sound of inhaled air, and comparing the velocity with an predetermined nominal value to verify the measured value of the velocity of sound $v_S$ of the air exhaled.

* * * * *